United States Patent
Annis et al.

(10) Patent No.: US 11,357,942 B1
(45) Date of Patent: Jun. 14, 2022

(54) INSERTION GUIDE FOR ENDOTRACHEAL TUBE

(71) Applicants: Jason Annis, Farmville, NC (US); Gregory Y. Lau, Las Vegas, NV (US)

(72) Inventors: Jason Annis, Farmville, NC (US); Gregory Y. Lau, Las Vegas, NV (US)

(73) Assignee: D R Burton Healthcare, LLC, Farmville, NC (US)

( * ) Notice: Subject to any disclaimer, the term of this patent is extended or adjusted under 35 U.S.C. 154(b) by 416 days.

(21) Appl. No.: 16/588,332

(22) Filed: Sep. 30, 2019

Related U.S. Application Data

(63) Continuation-in-part of application No. 15/420,284, filed on Jan. 31, 2017, now Pat. No. 10,434,272, and a continuation-in-part of application No. 15/340,469, filed on Nov. 1, 2016, now Pat. No. 10,426,908.

(51) Int. Cl.
*A61M 16/04* (2006.01)

(52) U.S. Cl.
CPC .... *A61M 16/0488* (2013.01); *A61M 16/0418* (2014.02)

(58) Field of Classification Search
None
See application file for complete search history.

(56) References Cited

U.S. PATENT DOCUMENTS

| | | | |
|---|---|---|---|
| 2,865,374 A | 12/1958 | Brown et al. | |
| 3,757,768 A | 9/1973 | Kline | |
| 3,802,440 A | 4/1974 | Salem et al. | |
| 4,244,362 A | 1/1981 | Anderson | |
| 4,960,122 A | 10/1990 | Mizus | |
| 5,058,577 A | 10/1991 | Six | |
| 5,183,031 A | 2/1993 | Rossoff | |
| 5,791,338 A | 8/1998 | Merchant et al. | |
| 5,842,973 A | 12/1998 | Bullard | |
| 5,897,489 A * | 4/1999 | Urbanowicz | A61B 1/0014 600/185 |
| 6,183,463 B1 | 2/2001 | Webster, Jr. | |
| 6,213,974 B1 | 4/2001 | Smith et al. | |
| 6,761,171 B2 | 7/2004 | Toti et al. | |
| D650,476 S | 12/2011 | Pecherer | |
| 8,499,763 B2 * | 8/2013 | Ledwith | A61M 16/0434 128/207.18 |
| 8,505,531 B2 | 8/2013 | Pecherer et al. | |
| 8,746,239 B2 | 6/2014 | Yoshida | |
| 9,010,320 B2 | 4/2015 | Furman et al. | |
| 10,149,957 B2 * | 12/2018 | Runnels | A61M 16/0488 |

* cited by examiner

*Primary Examiner* — Manuel A Mendez
(74) *Attorney, Agent, or Firm* — Tuggle Duggins P.A.; Blake P. Hurt

(57) ABSTRACT

An insertion guide facilitates insertion of an endotracheal tube (ETT) into the trachea of a patient instead of the esophagus of the patient. The ETT includes an elongated, somewhat flexible, generally hollow tube and the insertion guide includes an elongated, solid and relatively rigid shaft that is configured to be positioned within the hollow tube of the ETT. The shaft is provided with a radiused portion and/or an angled portion adjacent a distal end of the insertion guide that protrudes outwardly beyond a distal end of the ETT. The radiused portion and/or the angled portion of the shaft facilitate insertion of the distal end of the ETT past the epiglottis and into the trachea of the patient instead of into the esophagus of the patient.

18 Claims, 14 Drawing Sheets

INSERTION GUIDE FOR ENDOTRACHEAL TUBE

This is a continuation-in-part of and claims benefits under pending prior application Ser. No. 15/340,469 filed 1 Nov. 2016, now U.S. Pat. No. 10,426,908, and application Ser. No. 15/420,284 filed 31 Jan. 2017, now U.S. Pat. No. 10,434,272, which are both incorporated by reference in their respective entireties herein.

FIELD OF THE INVENTION

The invention disclosed herein pertains generally to devices, apparatus, systems, assemblies and methods for facilitating the insertion of an endotracheal tube (ETT) into the trachea of a patient. More particularly, the invention pertains to an insertion guide for an ETT. In exemplary embodiments, the insertion guide has a distal end that protrudes outwardly beyond a distal end of the ETT and is provided with a radiused portion and/or an angled portion at its distal end for atraumatic introduction of the distal end of the ETT into the trachea of the patient.

BACKGROUND AND DESCRIPTION OF THE PRIOR ART

Tracheal intubation, or simply intubation, involves the placement of a flexible plastic tube into the windpipe, or trachea, of a patient to establish and maintain an open airway for aspiration, ventilation, and/or the administration of certain drugs. Intubation may also be utilized to prevent asphyxiation or obstruction of the patient's airway. A flexible plastic tube referred to as a tracheal tube may be inserted into the trachea through the nose (gastrotracheal) or mouth (orotracheal) of the patient. In orotracheal intubation, a tracheal tube, and more specifically an endotracheal tube (ETT), is passed through the mouth, between the vocal cords, and into the trachea of the patient.

Orotracheal intubation requires sufficient skill to avoid inserting the ETT into the esophagus connecting the throat to the stomach of the patient rather than the trachea connecting the throat to the lungs of the patient. The epiglottis is an upwardly extending flap of elastic cartilage tissue that is attached to the entrance of the larynx. During breathing, the epiglottis is open to penult ventilation, while during swallowing the epiglottis closes to prevent pulmonary aspiration and to direct ingested liquids and/or solids into the esophagus leading to the stomach. Although the epiglottis is generally open at the time of orotracheal intubation, care must still be exercised to insert the distal end of the ETT into the trachea instead of the esophagus. In particular, the distal end of the ETT must be guided past the tip of the epiglottis and into the trachea, taking care not to traumatically impact the corniculate cartilage and/or surrounding tissue in the process.

Orotracheal intubation may be facilitated by the use of a laryngoscope, a video laryngoscope, a flexible fiber optic bronchoscope, or the like, to identify the vocal cords and to pass the ETT between them and into the trachea of the patient rather than into the esophagus. Despite the availability of such insertion facilitating equipment, a relatively high degree of difficulty remains and an individual inserting an ETT must be suitably skilled and experienced to ensure that the distal end of the ETT is guided into the trachea. Furthermore, orotracheal intubation is oftentimes performed in a medical emergency by an emergency medical technician (EMT) and/or under circumstances in which specialized insertion facilitating equipment is not readily available. Improper insertion of an ETT can lead to pulmonary aspiration of stomach contents into the lungs of a patient, which can result in serious complications from chemical aspiration pneumonitis. More importantly, unintended and unrecognized insertion of the ETT into the esophagus of the patient can lead to potentially fatal anoxia.

In view of the foregoing, it is apparent that a need exists for an improved apparatus, device, system, assembly and/or method for facilitating the insertion of an ETT into the trachea of a patient. More specifically, a need exists for an insertion guide for an ETT. A further and more particular need exists for an insertion guide for performing an orotracheal intubation that reduces the difficulty and the degree of training required of an individual to insert an ETT into the trachea of a patient instead of into the esophagus of the patient. A still further need exists for an insertion guide for performing an orotracheal intubation in a medical emergency and/or under circumstances in which specialized insertion facilitating equipment is not available.

In response to the aforementioned disadvantages and needs, the present invention was conceived and has as an objective to provide an insertion guide for facilitating the insertion of an ETT into the trachea of a patient instead of into the esophagus of the patient.

The present invention has as a further objective to provide an insertion guide for an ETT that reduces the difficulty and the level of skill and experience required of an individual to perform an orotracheal intubation.

The present invention has as yet a further objective to provide an insertion guide for performing an orotracheal intubation in a medical emergency and/or under circumstances in which specialized insertion facilitating equipment is not available.

The present invention has an additional objective to provide an insertion guide for an ETT that is removable via a notch formed in the handle collar.

The present invention has as yet a further objective to provide an insertion guide for an ETT that facilitates the removal of the guide via an O-ring positioned within the handle.

The present invention has as yet another objective to provide an insertion guide for an ETT that defines an annular protuberance defined within the handle that serves as a seat for said O-ring.

Other objectives and advantages of the present invention will become readily apparent to and appreciated by those skilled in the art as a more detailed description of exemplary embodiments of the invention is set forth below.

SUMMARY OF THE INVENTION

The aforementioned objectives and advantages, as well as other objectives and advantages not expressly set forth herein, are realized by providing an insertion guide for facilitating insertion of an endotracheal tube (ETT) into the trachea of a patient according to the present invention, as disclosed by the exemplary embodiments shown and described herein.

In one aspect, the present invention is embodied by an insertion guide for facilitating insertion of an endotracheal tube (ETT) into the trachea of a patient that includes an elongated shaft made of a relatively rigid material and having at least one of a radiused portion and an angled portion adjacent a distal end of the insertion guide. The shaft of the insertion guide is configured for insertion within a hollow, flexible tube of the ETT to guide a distal end of the ETT into the trachea of the patient. In one embodiment, the shaft of the insertion guide includes a solid metallic core having a polymeric outer covering. In another embodiment, the insertion guide includes a solid metallic core having a rubberized outer covering. In another embodiment, an outer diameter of the shaft of the insertion guide is between about 3 mm and about 5 mm. In yet another embodiment, the radiused portion of the shaft of the insertion guide has a predetermined curvature that is greater than the curvature of the tube of the ETT adjacent the distal end of the ETT. In another embodiment, the curvature of the radiused portion of the shaft of the insertion guide is selected to be complementary to the curvature of the larynx in the region of the entrance to the trachea of the patient. In another embodiment, the distal end of the insertion guide protrudes beyond the distal end of the ETT. In another embodiment, the angled portion of the shaft of the insertion guide serves to guide the tube of the ETT past the epiglottis and into the trachea of the patient.

In another aspect, the present invention is embodied by a combination endotracheal tube (ETT) and insertion guide for facilitating insertion of the ETT into the trachea of a patient. The combination includes an ETT including an elongated, generally hollow tube made of a flexible material, and an insertion guide including an elongated shaft made of a relatively rigid material. The shaft of the insertion guide is provided with a radiused portion having a curvature adjacent a distal end of the insertion guide. The relatively rigid shaft of the insertion guide is inserted within the hollow, flexible tube of the ETT such that a curvature of the tube adjacent the distal end of the ETT conforms to the curvature of the shaft adjacent the distal end of the insertion guide. In one embodiment, the curvature of the radiused portion of the shaft of the insertion guide is selected to be complementary to the curvature of the larynx in the region of the entrance to the trachea of the patient. In another embodiment, the distal end of the insertion guide protrudes beyond the distal end of the ETT. In another embodiment, the shaft of the insertion guide further includes an angled portion adjacent the distal end of the insertion guide that serves to guide the tube of the ETT past the epiglottis and into the trachea of the patient.

In yet another aspect, the present invention is embodied by a method for facilitating the insertion of an endotracheal tube (ETT) into the trachea of a patient instead of into the esophagus of the patient. The method includes providing an ETT including an elongated, generally hollow tube made of a flexible material, the ETT having a proximal end and a distal end. The method further includes providing an insertion guide including an elongated shaft made of a relatively rigid material, the insertion guide having a proximal end and a distal end. The method further includes positioning the shaft of the insertion guide within the tube of the ETT such that the distal end of the insertion guide protrudes beyond the distal end of the ETT. The method further includes passing the distal end of the insertion guide positioned within the tube of the ETT through the mouth and vocal cords of the patient to guide the distal end of the ETT into the trachea of the patient. In one embodiment, the distal end of the insertion guide protrudes beyond the distal end of the ETT, and the shaft is provided with a radiused portion adjacent the distal end of the insertion guide having a curvature that is greater than a curvature of the tube adjacent the distal end of the ETT. In another embodiment, the curvature of the tube of the ETT conforms to the curvature of the radiused portion of the shaft of the insertion guide when the shaft of the insertion guide is positioned within the tube of the ETT. In another embodiment, the distal end of the insertion guide protrudes beyond the distal end of the ETT, and the shaft further includes an angled portion adjacent the distal end of the insertion guide.

In an alternative aspect, the present invention is embodied by an insertion guide for facilitating insertion of an endotracheal tube (ETT) into the trachea of a patient that includes an elongated shaft made of a relatively rigid material and having at least one of a radiused portion and an angled portion adjacent a distal end of the insertion guide. The shaft of the insertion guide is configured for insertion within a hollow, flexible tube of the ETT to guide a distal end of the ETT into the trachea of the patient. In one embodiment, the shaft of the insertion guide includes a solid metallic core having a polymeric outer covering. In another embodiment, the insertion guide includes a solid metallic core having a rubberized outer covering. In another embodiment, an outer diameter of the shaft of the insertion guide is between about 3 mm and about 5 mm. In yet another embodiment, the radiused portion of the shaft of the insertion guide has a predetermined curvature that is greater than the curvature of the tube of the ETT adjacent the distal end of the ETT. In another embodiment, the curvature of the radiused portion of the shaft of the insertion guide is selected to be complementary to the curvature of the larynx in the region of the entrance to the trachea of the patient. In another embodiment, the distal end of the insertion guide protrudes beyond the distal end of the ETT. In another embodiment, the angled portion of the shaft of the insertion guide serves to guide the tube of the ETT past the epiglottis and into the trachea of the patient. In another embodiment, a handle is defined at the proximate end of the insertion guide, the handle including a port and a channel passing through the handle, and channel terminating at the bottom of the handle more proximate the distal end of the insertion guide relative to the port. An oxygen connection may be engaged via the port, and oxygen flows through the channel and out the distal portion of the handle, allowing a medical service provider to perform apneic oxygenation technique with the ETT positioned at the tracheal opening.

In one or more alternative aspects, the present invention is embodied by an insertion guide for facilitating insertion of an endotracheal tube (ETT) into the trachea of a patient that includes an elongated shaft made of a relatively rigid material and having at least one of a radiused portion and an angled portion adjacent a distal end of the insertion guide. The shaft of the insertion guide is configured for insertion within a hollow, flexible tube of the ETT to guide a distal end of the ETT into the trachea of the patient. In one embodiment, the shaft of the insertion guide includes a solid metallic core having a polymeric outer covering. In another embodiment, the insertion guide includes a solid metallic core having a rubberized outer covering. In yet another embodiment, an outer diameter of the shaft of the insertion guide is between about 3 mm and about 5 mm. In a further embodiment, the radiused portion of the shaft of the insertion guide has a predetermined curvature that is greater than the curvature of the tube of the ETT adjacent the distal end of the ETT. One or more of these embodiments define the curvature of the radiused portion of the shaft of the insertion guide is selected to be complementary to the curvature of the larynx in the region of the entrance to the trachea of the patient. In an embodiment, the distal end of the insertion guide protrudes beyond the distal end of the ETT. As such, the angled portion of the shaft of the insertion guide serves to guide the tube of the ETT past the epiglottis and into the trachea of the patient. In one or more embodiment, a handle is defined at the proximate end of the insertion guide, the handle including a port and a channel passing through the handle, and channel terminating at the bottom of the handle more proximate the distal end of the insertion guide relative to the port. An oxygen connection may be engaged via the port, and oxygen flows through the channel and out the distal portion of the handle, allowing a medical service provider to perform apneic oxygenation technique with the ETT positioned at the tracheal opening. The handle further defines a notch formed in the handle collar that frictionally engages a terminal, proximal end of the ETT. In order to better facilitate the quick and efficient release of the handle from the ETT, ideally requiring no more than a single hand of a user, the handle may additionally define an annular protuberance extending from the interior diameter of the handle. A resilient member such as a rubber O-ring preferably seats abutting the protuberance so as to facilitate the effective mating of the "female" coupling of the handle to the ETT while also permitting the efficient removal of the intubation guide from the ETT as described above.

BRIEF DESCRIPTION OF THE DRAWINGS

The aforementioned aspects, objects, features, advantages and exemplary embodiments of the present invention will be more fully understood and appreciated by those skilled in the art when considered in conjunction with the accompanying drawing figures, in which like reference characters designate the same or similar parts throughout the several views.

DESCRIPTION OF EXEMPLARY EMBODIMENTS OF THE INVENTION

Figure 1:
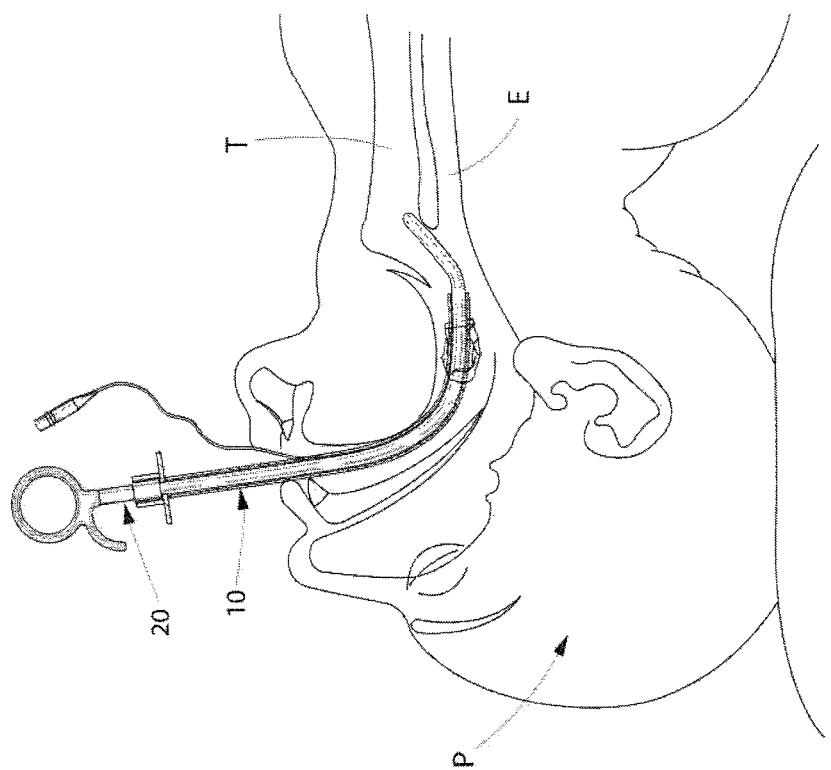
FIG. 1 is an environmental view illustrating an endotracheal tube (ETT) and an insertion guide for facilitating insertion of the ETT into the trachea of a patient in accordance with an exemplary embodiment of the present invention.

For a better understanding of the present invention and its operation, turning now to the drawing figures, FIG. 1 is an environmental elevated side view illustrating an endotracheal tube (ETT), indicated generally by reference character 10, and an insertion guide (also known as a stylus), indicated generally by reference character 20, for facilitating insertion of the ETT into the trachea T of a patient P. The ETT 10 shown and described herein for purposes of illustration and not limitation, is a conventional ETT configured for tracheal intubation, and more particularly, orotracheal intubation of the patient P. Orotracheal intubation is performed to establish and maintain an open airway for ventilation of the patient P and/or to administer certain drugs to the patient, for example by inhalation. As illustrated in FIG. 1, orotracheal intubation is accomplished by passing the ETT through the mouth and vocal cords and into the trachea T, commonly referred to as the windpipe, within the throat and neck area of the patient P. The distal end of the ETT must be guided past the tip of the epiglottis attached to the entrance of the larynx and into the trachea T leading to the lungs (bronchi) of the patient P instead of into the esophagus E leading to the stomach of the patient. In most instances, the patient P is in a supine position when an orotracheal intubation is performed and the head of the patient may be tilted backwards somewhat to better align the trachea T with the vocal cords of the patient P. Regardless, it remains relatively difficult to locate the trachea T in its more anterior orientation and a degree of skill and experience is required of an individual to perform a proper orotracheal intubation. An insertion guide 20 constructed in accordance with the present invention, is intended to facilitate insertion of an ETT into the trachea T of a patient. However, it is not intended by this disclosure of exemplary embodiments to limit the configuration of the insertion guide 20 to the particular embodiments shown and described herein. Instead, it is expected that those of ordinary skill in the art will readily understand and appreciate that an insertion guide 20 according to the present invention may be constructed of various different materials in various different configurations and in various ways without departing from the general concepts and objectives of the present invention in any meaningful manner. As such, the scope of the present invention should be broadly construed in light of this disclosure and limited only by the appended claims.

Figure 2:
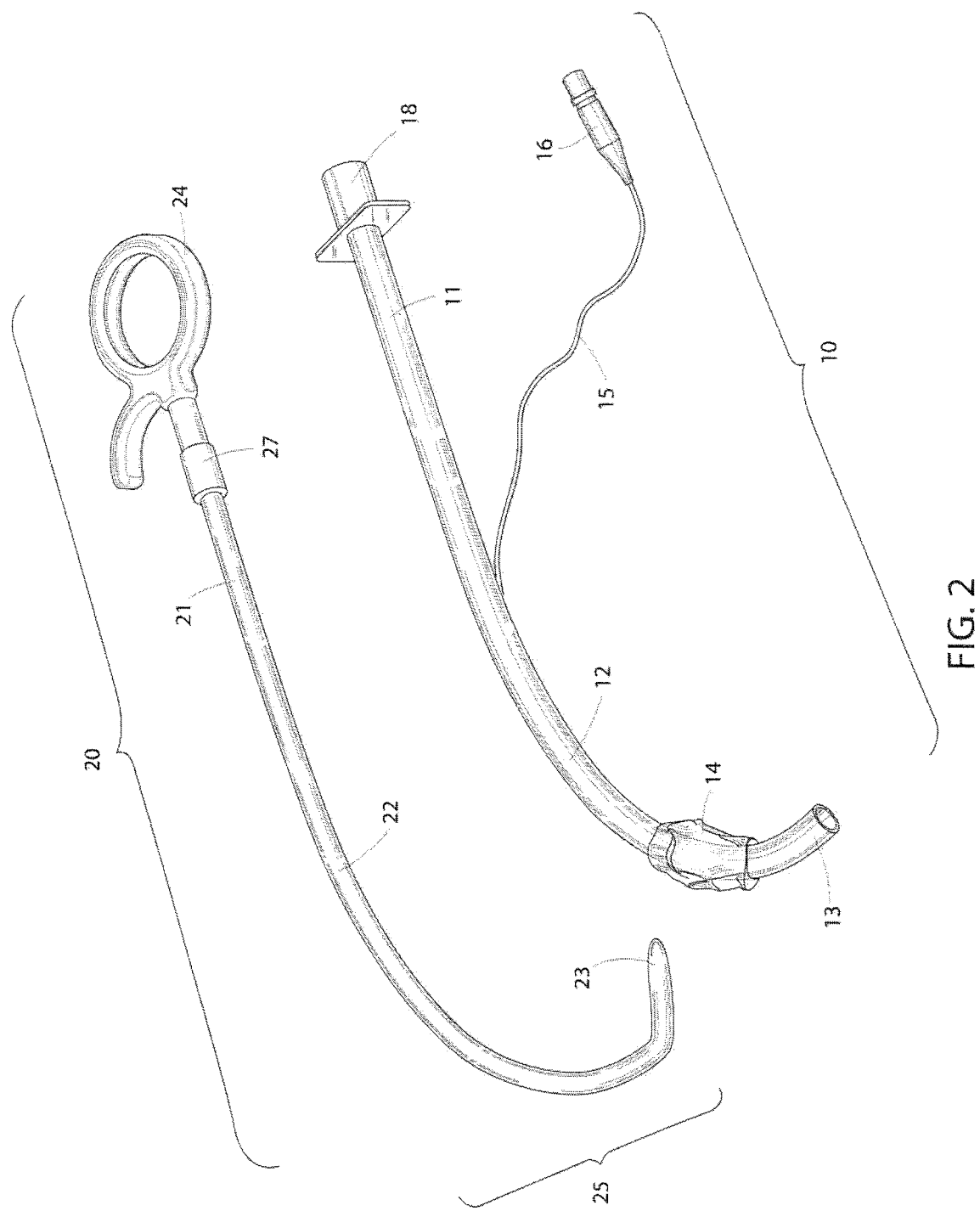
FIG. 2 is a perspective view showing the ETT and the insertion guide of FIG. 1 in greater detail.
Figure 3:
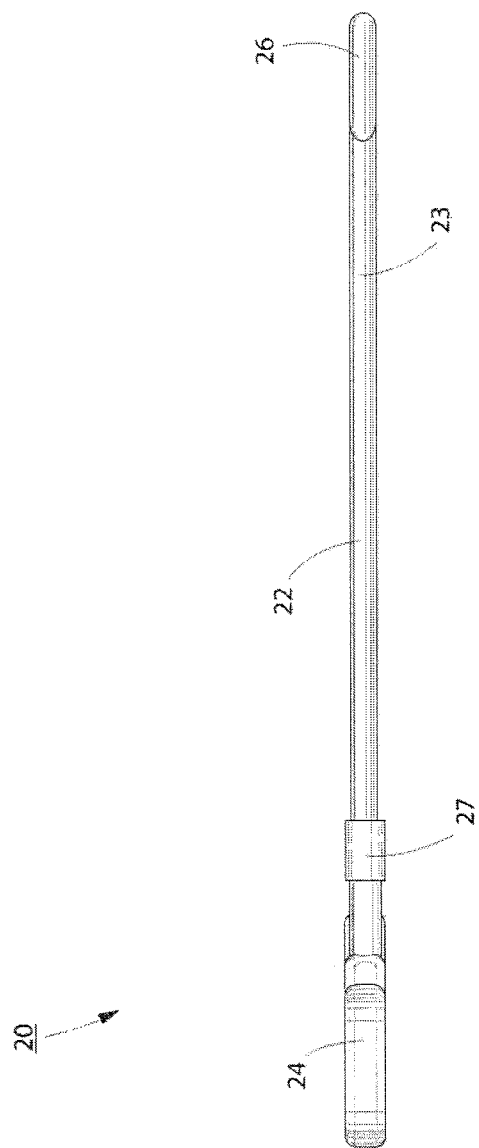
FIG. 3 is a plan front view of the insertion guide shown in FIG. 2.
Figure 4:
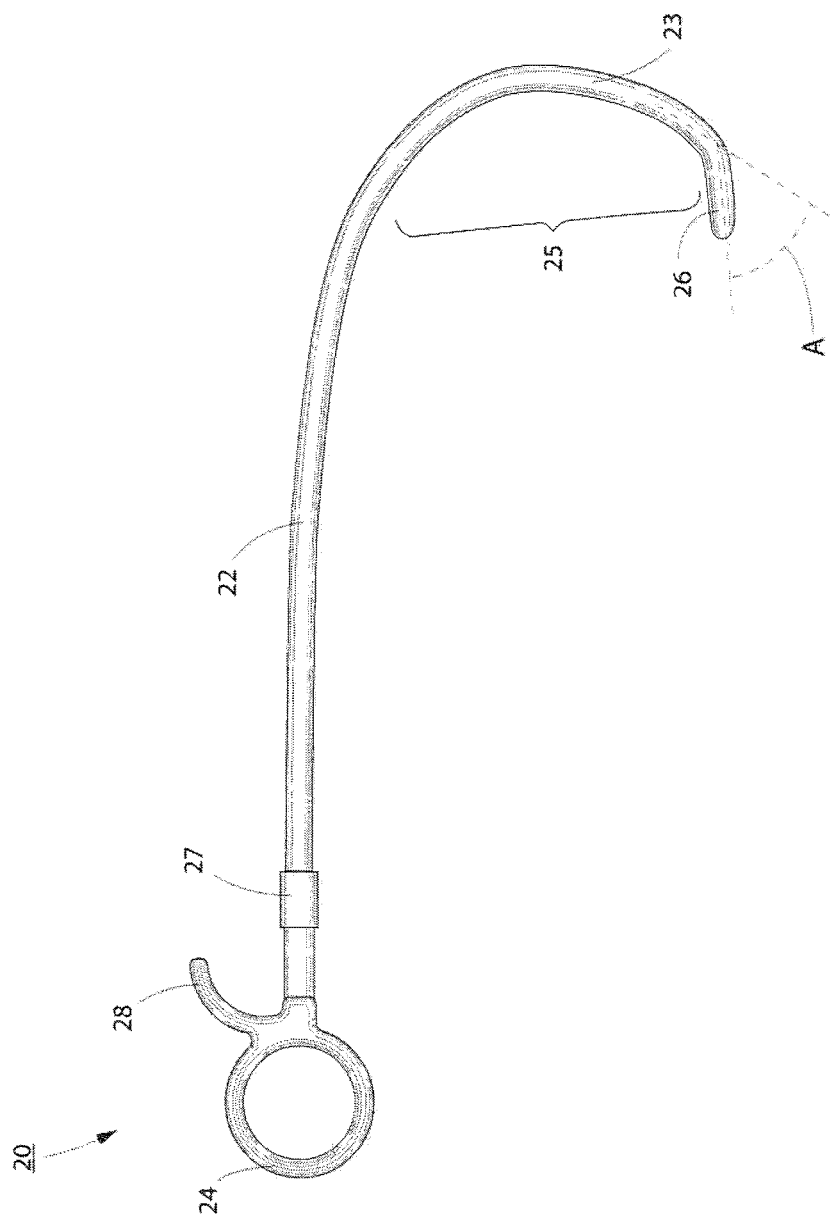
FIG. 4 is an elevation side view of the insertion guide shown in FIG. 2.
Figure 5:
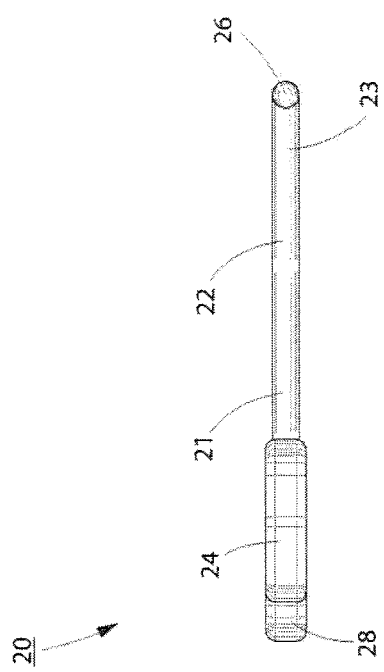
FIG. 5 is a top view of the insertion guide shown in FIG. 2.
Figure 6:
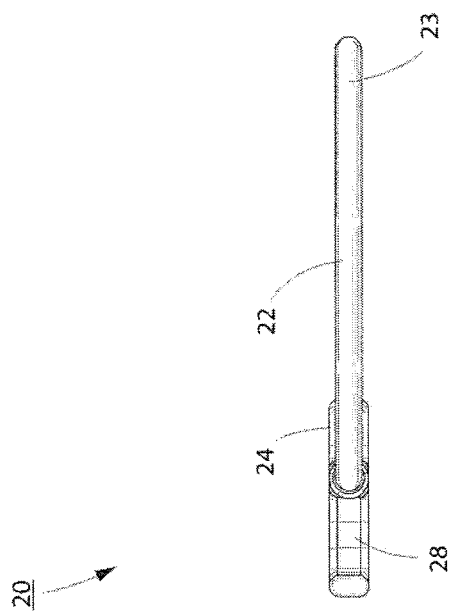
FIG. 6 is a bottom view of the insertion guide shown in FIG. 2.
Figure 7:
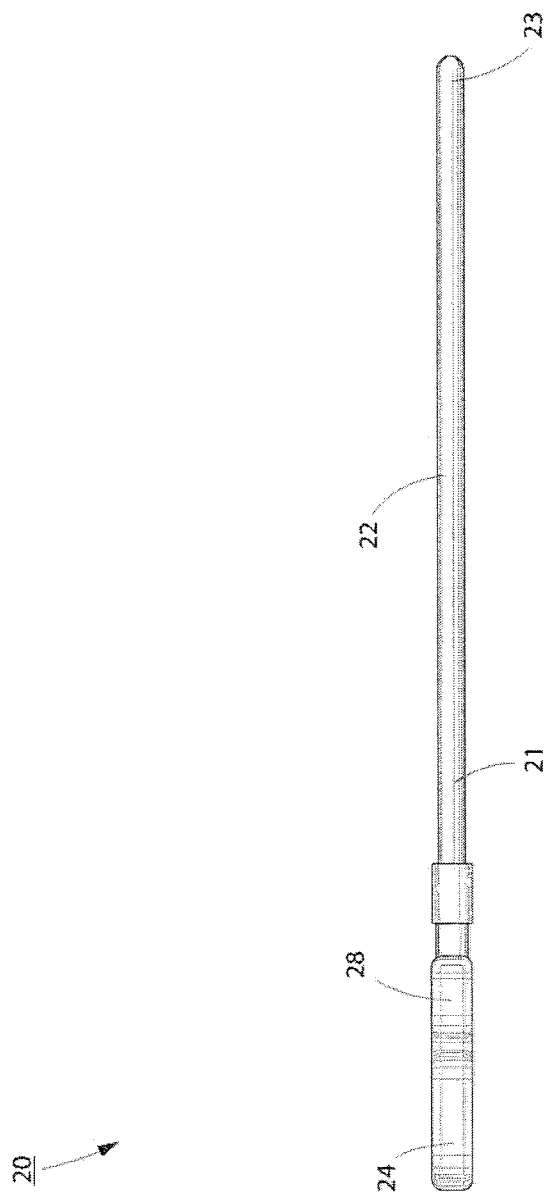
FIG. 7 is a plan rear view of the insertion guide shown in FIG. 2.

FIG. 2 shows a perspective view of ETT 10 and the insertion guide 20 illustrated by FIG. 1 in greater detail. FIGS. 3-7 provide various orthographic views (i.e. top, bottom, front, rear, and side views) of the insertion guide 20 shown in FIG. 2. By way of example only and not limitation, the ETT 10 comprises an elongated, somewhat flexible (i.e. defining a modulus of flexibility less than 50% that of insertion guide 20), generally hollow tube 12, typically made of a moderately rigid plastic material, such as polyvinyl chloride (PVC). As shown in FIG. 2, the tube 12 of the ETT 10 has a proximal end 11 and a distal end 13 that is configured to be inserted into the trachea T of a patient P, as previously described. A typical ETT 10 is available in various sizes. A common size of an ETT 10 suitable for use with an adult patient P has an inner diameter of between 7 and 8 mm and an outer diameter of about 8.8 mm, and is between about 22 and about 28 cm in length measured from the distal end 13 of the tube 12. The distal end 13 of the tube 12 may be cut perpendicular to the lengthwise axis of the tube 12 (as shown) or may be angled relative to the lengthwise axis so as to provide a bevel at the distal end 13 for better visualization of the vocal cords of the patient P during insertion.

The ETT 10 regularly comprises an inflatable balloon cuff 14 adjacent the distal end 13 of the tube 12 to provide a seal against the wall of the trachea T and thereby prevent leakage of respiratory gases and to protect the trachea T from intrusion of foreign matter, such as food particles, liquids and/or stomach acid, while the patient P is intubated. The balloon cuff 14 is deflated during insertion of the ETT 10 and is inflated after insertion through a pilot line 15 having a one-way valve 16 adapted to be connected to a source of pressurized air, such as a syringe and plunger (not shown), for remotely inflating the cuff. Although not shown, the pilot line 15 may further comprise a pilot balloon for indicating whether the balloon cuff 14 is sufficiently inflated. The ETT 10 further comprises a connector 18 at the proximal end 11 adapted for connecting the airway of the patient P to an anesthesia breathing circuit, a bag valve breathing mask or a mechanical ventilator. Connector 18 is of a universally standard size, and serves as the connection point for a shoulder of insertion guide proximal end 21 as will be described in further detail below. Also not shown, the ETT 10 may have an opening, commonly referred to as a "Murphy Eye" between the balloon cuff 14 and the distal end 13 of the tube 12 that functions as a vent and allows airflow in the event that the opening at the distal end 13 of the tube 12 is obstructed, for example if the end of the tube becomes lodged against the wall of the trachea T. If desired, the tube 12 of the ETT 10 may also be provided with a radiopaque line or other feature for locating the ETT on a radiograph.

The insertion guide 20 likewise has a proximal end 21 and a distal end 23. The preferred embodiment of insertion guide 20 includes cylindrical shoulder 27 that is sized and shaped to be received within connector 18, and form a frictional fit therewith upon insertion. Insertion guide 20 comprises an elongated, solid and relatively rigid (i.e. defining a modulus of flexibility greater than 50% that of ETT 10) shaft 22 that extends between the proximal end 21 and the distal end 23. If desired, the shaft 22 may be constructed of a unitary material, such as metal (e.g., aluminum, stainless steel, etc.) or plastic. Preferably, however, the shaft 22 of the insertion guide 20 may comprise a metallic inner core that is at least partially covered or encased by a polymeric material, such as polyethylene, polypropylene or the like. Alternatively, the metallic inner core of the shaft 22 may be covered by a rubberized material. Regardless, it is desirable for the outer surface of the shaft 22 to be smooth and free of any significant protuberances so as to permit introduction and advancement of the insertion guide 20 through the hollow ETT 10, as will be described. Accordingly, the shaft 22 of the insertion guide 20 has an outer diameter that is somewhat smaller than the inner diameter of the tube 12 of the ETT 10. By way of example only and not limitation, the outer diameter of the shaft 22 of the insertion guide 20 may be between about 3 mm and about 5 mm.

Referring in addition to FIGS. 3-7, insertion guide 20 further comprises a handle 24 securely attached to the shaft 22 adjacent the proximal end 21 of the insertion guide. Handle 24 preferably defines an annular shape for easy, single-handed manipulation and may be attached to the shaft 22 of the insertion guide 20 in any suitable manner, for example by an adhesive or tight press fit. Furthermore, handle 24 may be configured to be rotatable relative to shaft 22 or removable from shaft 22 for a desired purpose. A preferred embodiment of handle 24 also includes projection 28 that protrudes from the main body of handle 24 and serves as an alternative or secondary surface for removing insertion guide 20 from ETT 10, for example via the thumb of a user. Regardless, handle 24 is adapted to facilitate insertion of the insertion guide 20 and ETT 10 into the trachea T of the patient P and to thereafter facilitate removal of the insertion guide 20 from the trachea T and the ETT 10. The distal end 23 of shaft 22 has a predetermined curvature within a portion 25 of the shaft 22 that is selected to be complementary to the curvature of the larynx in the region of the entrance to the trachea T of the patient P. In addition, the tip of the shaft 22 at the distal end 23 of the insertion guide 20 preferably has an angled portion 26 for a purpose to be described in greater detail hereafter.

Referring again to the illustration of FIG. 1, the insertion guide 20 is inserted within the hollow tube 12 of the ETT 10 by positioning the proximal end 11 of the ETT 10 over the distal end 23 of the insertion guide 20 and moving (i.e., sliding, inserting, or otherwise displacing) the flexible plastic tube 12 of the ETT 10 along the length of the relatively rigid shaft 22 of the insertion guide 20. The tube 12 is advanced on the shaft 22 until the shoulder 27 of insertion guide 20 is mated within connector 18 of the ETT 10 and the distal end 23 of the insertion guide 20 protrudes beyond the distal end 13 of the ETT 10. In particular, the distal end 23 of the shaft 22 of the insertion guide 20 extends outwardly from the distal end 13 of the ETT 10. Furthermore, the distal end 13 of the ETT 10 conforms to the curvature of the radiused portion 25 of the shaft 22 of the insertion guide 20. Consequently, the distal end 13 of the ETT 10 follows the curvature of the radiused portion 25 of the insertion guide 20 that is complementary to the curvature of the larynx at the entrance to the trachea T. As a result, the distal end 13 of the ETT 10 is more easily introduced without trauma into the trachea T of the patient P instead of the esophagus E of the patient. The angled portion 26 of the shaft 22 at the distal end 23 of the insertion guide 20 further serves to guide the shaft 22, and consequently, the distal end 13 of the ETT 10, past the epiglottis and into the trachea T of the patient P (see Angle A in FIG. 4). In this embodiment, angled portion 26 combine with rigid shaft 22 to provide a more anatomically correct curve upon insertion of flexible ETT 10. This curve, facilitated by angled portion 26, aids in the placement of ETT 10 more anteriorly towards the tracheal opening as shown in FIG. 1. This is especially true when using video laryngoscopes which include very large laryngeal blades with significant curvatures (not shown). One of the goal of insertion guide 20 is to mimic the curvature of conventional video scopes, thus making the passage of ETT 10 into the trachea T easier, faster, and less likely to cause trauma.

In the exemplary embodiments shown and described herein, the radiused portion 25 of the relatively rigid shaft 22 of the insertion guide 20 has a curvature that is greater than the curvature of the more flexible tube 12 of the ETT 10. Accordingly, the curvature at the distal end 13 of the ETT 10 conforms to the curvature of the radiused portion 25 of the shaft 22 of the insertion guide 20 when the shaft 22 of the insertion guide 20 is positioned within the tube 12 of the ETT 10. In one embodiment, the curvature of the radiused portion 25 of the shaft 22 is at least about five degrees (5°). In another embodiment, the curvature of the radiused portion 25 of the shaft 22 ranges between about five degrees (5°) and about seven degrees (7°). Furthermore, the distal end 23 of the insertion guide 20 protrudes outwardly beyond the distal end 13 of the ETT 10. In one embodiment, the distal end 23 of the insertion guide 20 protrudes beyond the distal end 13 of the ETT 10 by at least about 25 mm. Still further, the shaft 22 of the insertion guide 20 may be provided with an angled portion 26 at the distal end 23 of the insertion guide 20 that serves to guide the tube 12 of the ETT 10 past the epiglottis and into the trachea T of the patient P. In one embodiment, the angled portion 26 of the shaft 22 of the insertion guide 20 has a length of at least about 25 mm. In another embodiment, the angled portion 26 of the shaft 22 of the insertion guide 20 has a slope of at least about 0.20.

As will be readily understood and apparent to those having ordinary skill in the relevant art, an ETT 10 and an insertion guide 20 according to the present invention provides a number of advantages over existing devices, apparatus, systems, assemblies and methods for facilitating insertion of an ETT into the trachea T of a patient P. By way of example only and not limitation, the insertion guide 20 having a proximal end 21 and a distal end 23 and comprising an elongated, relatively rigid shaft 22 that is provided with a radiused portion 25 and/or an angled portion 26 adjacent the distal end 23 of the insertion guide 20 facilitates atraumatic insertion of the ETT 10 into the trachea T of the patient P instead of into the esophagus E of the patient P.

Figure 8:
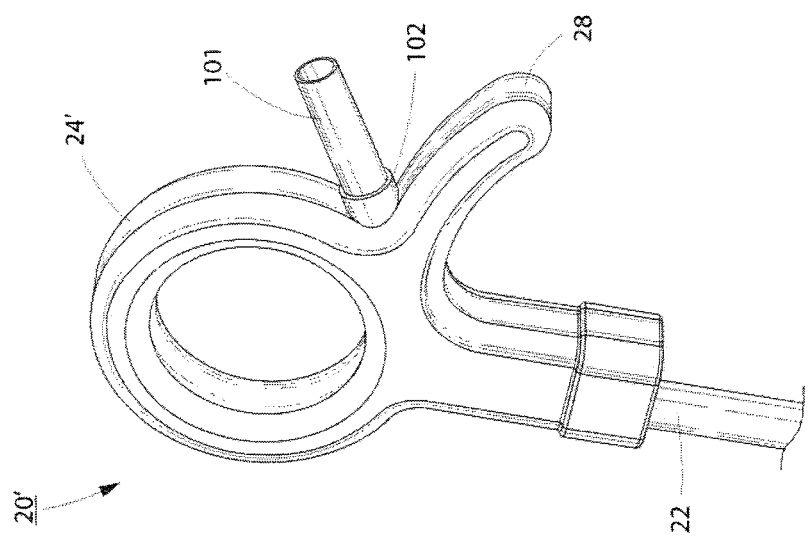
FIG. 8 is a perspective view of an alternative embodiment of an insertion guide.
Figure 9:
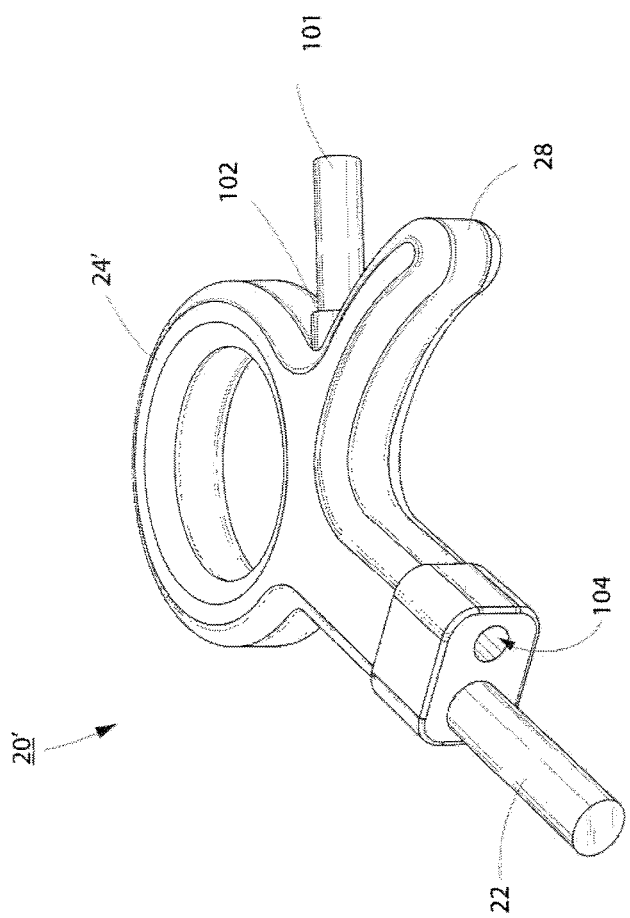
FIG. 9 is a perspective view of the insertion guide shown in FIG. 8.
Figure 10:
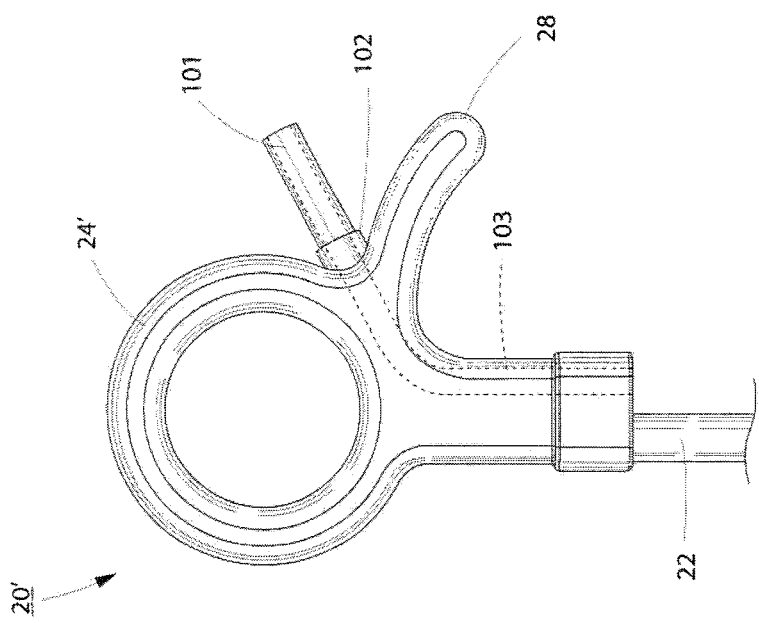
FIG. 10 is a plan view of the insertion guide shown in FIG. 8.

FIGS. 8-10 demonstrate an alternate embodiment of insertion guide 20', for use with ETT 10 (not shown) as described above. As would be understood, gases flow down their respective concentration gradients. The air humans breathe has a higher concentration of oxygen than the tissues that metabolize it. This means the oxygen in the air inside the lungs of a human is readily absorbed by the alveoli, flows through the human blood stream, diffuses into the body's tissues and is converted into carbon dioxide. Because this process converts the oxygen into a different molecule (carbon dioxide), the oxygen will keep moving forward in this cycle as long as the lungs contain oxygen, blood is circulating, and tissues are consuming it. As previously described, intubating a patient, particularly a very young, very old, or very obese patient, can carry numerous risks, not the least of which is that the patient may stop breathing, a condition known as apnea. In order to offset the dangerous results of apnea, including brain damage and death, it may be desirable to continuously administer oxygen during the apneic period, a practice knowns as apneic oxygenation. Research has illustrated that apneic oxygenation can safely prolong the duration of apnea without desaturation of oxygen in the bloodstream, viewed as a vital buffer in problematic intubations when even seconds can make the difference between a routine procedure and damage to the patient.

FIG. 8 is a perspective view of an upper portion of insertion guide 20' defining port 101 extending from handle 24' and FIG. 9 is a perspective view of a lower portion of the same structure. Handle 24' preferably defines an annular shape for easy, single-handed manipulation and may be attached to the shaft 22 of the insertion guide 20' in any suitable manner, for example by an adhesive or tight press fit. Furthermore, handle 24' may be configured to be rotatable relative to shaft 22 or removable from shaft 22 for a desired purpose. A preferred embodiment of handle 24' also includes projection 28 that protrudes from the main body of handle 24' and serves as an alternative or secondary surface for removing insertion guide 20' from ETT 10, for example via the thumb of a user. Port 101 preferably extends angularly from handle 24', for example at about a forty-five degree (45°) angle relative to the joint formed by projection 28 and handle 24'. Preferred port 101 defines a generally circular cross-section and cylindrical shape to facilitate efficient engagement with conventional tubing (not shown) for use in flowing oxygen from a reservoir such as an oxygen tank into port 101. An embodiment of port 101 may further include annular cuff or shoulder 102 with a slightly larger circumference but an otherwise complementary shape to that of port 101 to ensure that little to no oxygen inadvertently flows out the base of the tubing when connected to port 101.

FIG. 10 is a plan view of the insertion guide 20' with the understanding that the opposing side would be a mirror image thereof. Port 101 is preferably in fluid communication with channel 103 (illustrated in dotted fashion) which permits the oxygen carried by port 101 to flow through handle 24' and fluidly exit via aperture 104 (see FIG. 9). Although channel 103 may take any number of shapes, sizes, and/or paths through handle 24', it is preferable that channel 103 connect port 101 and aperture 104 through a generally direct route, compensating for the curvature in handle 24' with a slightly arcuate shape. Once passed through channel 103, the oxygen exits the distal end of handle 24' via aperture 104 and flows down the longitudinal length of insertion guide 20' and ETT 10, facilitating the performance of one or more apneic oxygenation techniques with ETT 10 remaining positioned within the tracheal opening.

Figure 11:
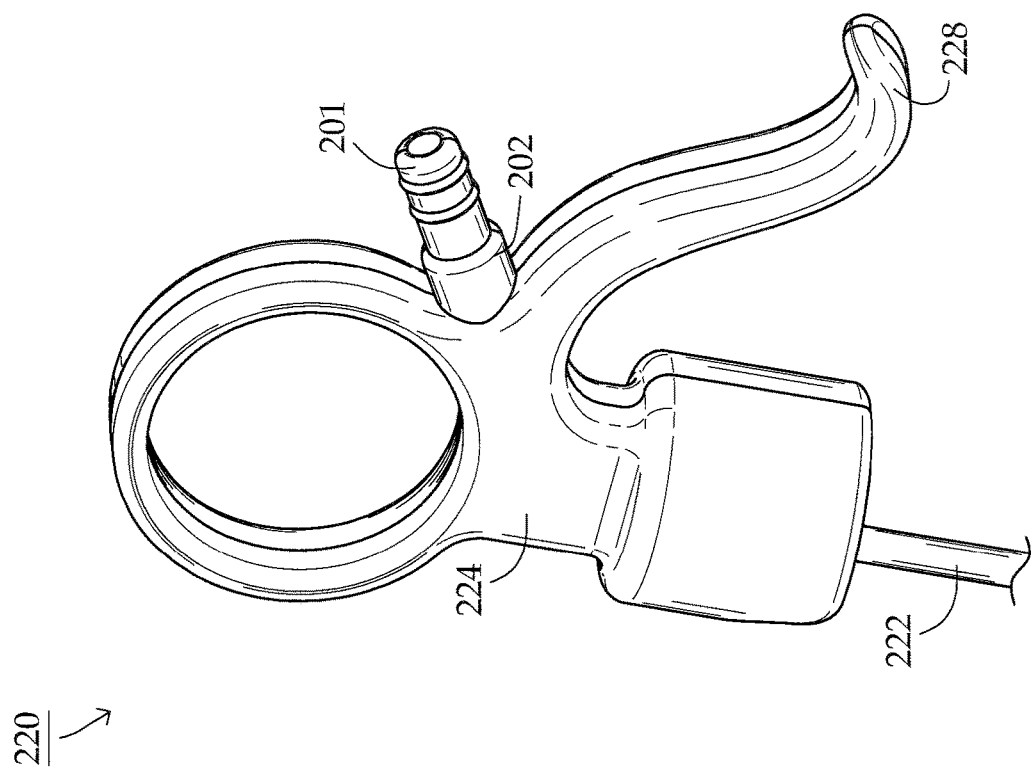
FIG. 11 is a perspective view of an alternative embodiment of an insertion guide.
Figure 12:
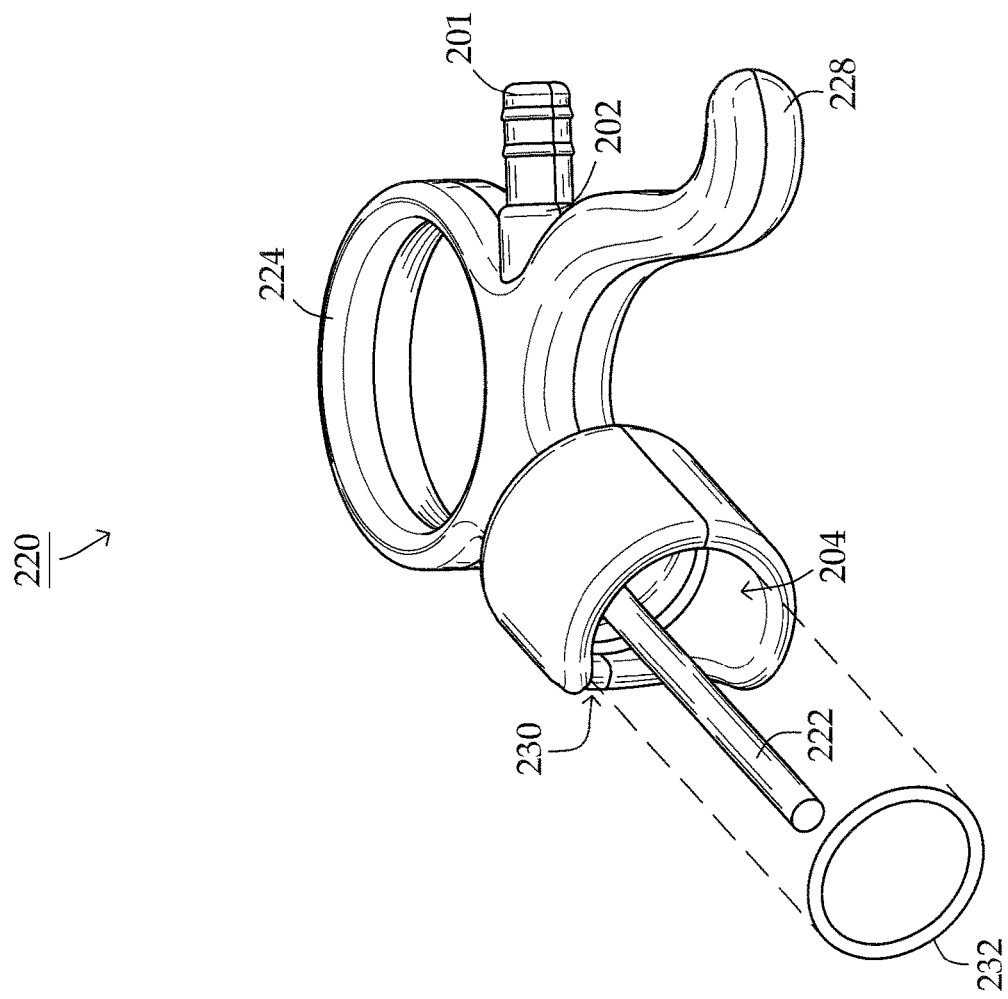
FIG. 12 is a perspective view of the insertion guide of FIG. 11 with an O-ring exploded therefrom.
Figure 13:
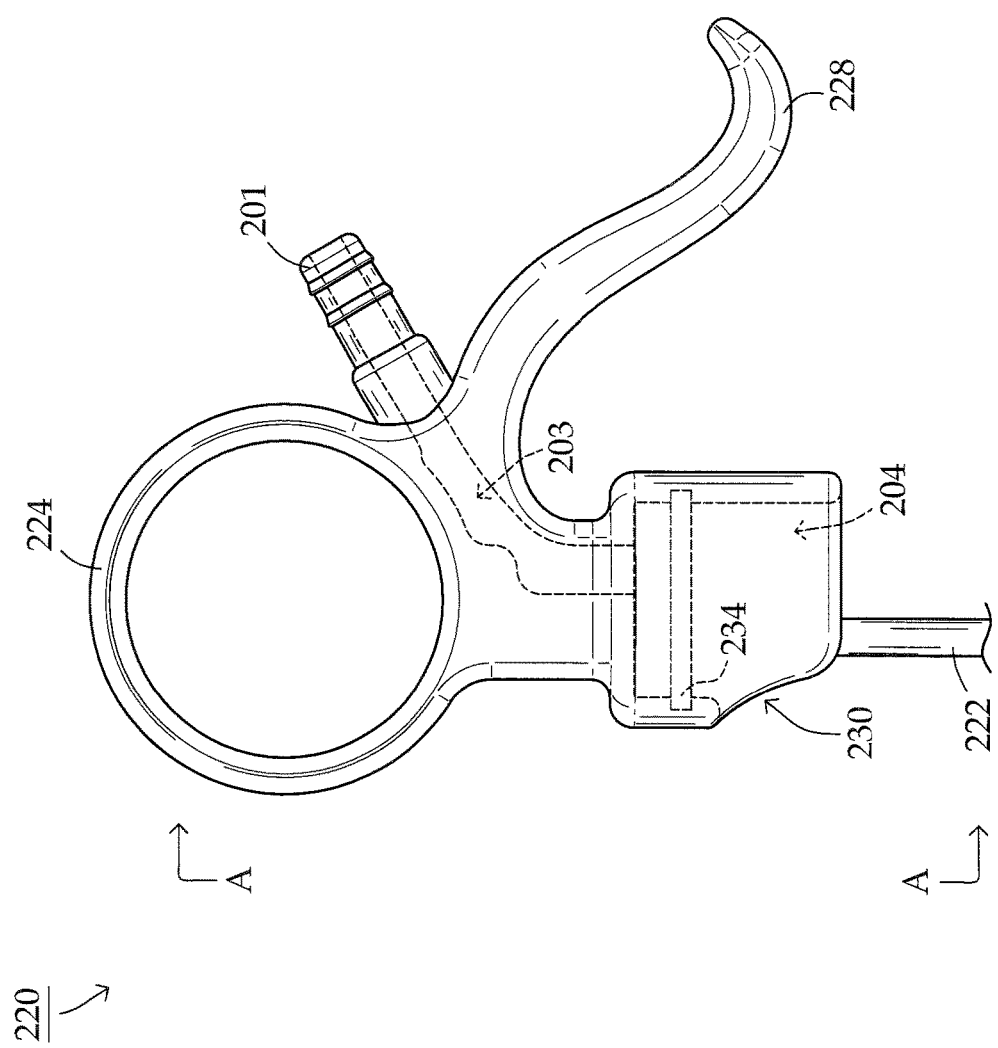
FIG. 13 is a plan view of the insertion guide shown in FIG. 11.
Figure 14:
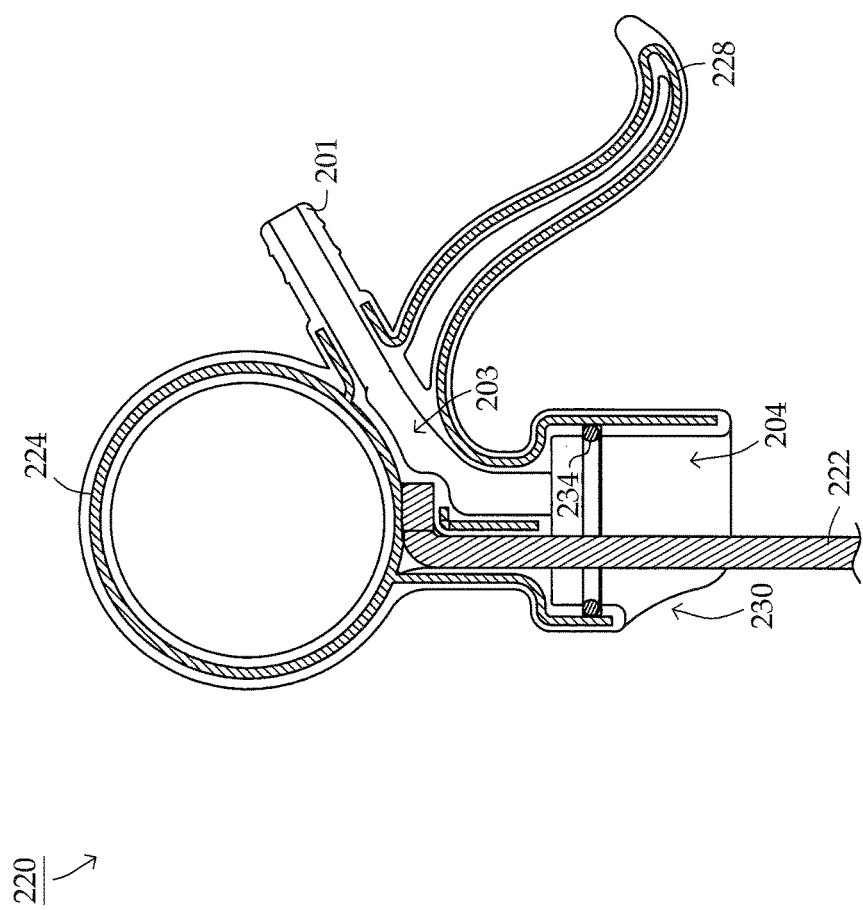
FIG. 14 is a cross-sectional view of the insertion guide as shown in FIG. 13.

FIGS. 11-14 demonstrate an alternative embodiment of insertion guide 220, similar in some respects to insertion guide 20 and 20' but including a modified handle as will be described in further detail below. FIG. 11 is a perspective view of an upper portion of insertion guide 220 defining port 201 extending from handle 224 and FIG. 12 is a perspective view of a lower portion of the same structure with O-ring 232 exploded therefrom, both Figures illustrating notch 230 defined in the bottom portion of handle 224. Handle 224 preferably defines an annular shape for easy, single-handed manipulation and may be attached to the shaft 222 of the insertion guide 220 in any suitable manner, for example by an adhesive or tight press fit. However, as demonstrated in the Figures handle 224 defines a "female" (as contrasted with "male") coupling to ETT 10 (not shown) so as to promote more universal application across various ETT styles and designs. A structural result of this configuration is that a large, central aperture 204 exists within the lower portion of handle 224 and is in communication with notch 230. As illustrated in FIGS. 12 and 14, preferred handle 224 for insertion guide 220 includes a deformable member, for example a rubber O-ring 232. A preferred embodiment of handle 224 also includes projection 228 that protrudes from the main body of handle 224 and serves as an alternative or secondary surface for removing insertion guide 220 from ETT 10, for example via the thumb of a user. Port 201 preferably extends angularly from handle 224, for example at about a forty-five degree (45°) angle relative to the joint formed by projection 228 and handle 224. Preferred port 201 defines a generally circular cross-section and cylindrical shape to facilitate efficient engagement with conventional tubing (not shown) for use in flowing oxygen from a reservoir such as an oxygen tank into port 201. An embodiment of port 201 may further include annular cuff or shoulder 202 with a slightly larger circumference but an otherwise complementary shape to that of port 201 to ensure that little to no oxygen inadvertently flows out the base of the tubing when connected to port 201.

FIG. 13 is a plan view of the insertion guide 220 with the understanding that the opposing side would be a mirror image thereof. Port 201 is preferably in fluid communication with channel 203 (illustrated in dotted fashion) which permits the oxygen carried by port 201 to flow through handle 224 and fluidly exit via aperture 204 (see FIG. 12). Although channel 203 may take any number of shapes, sizes, and/or paths through handle 224, it is preferable that channel 203 connect port 201 and aperture 204 through a generally direct route, compensating for the curvature in handle 224 with a slightly arcuate shape. Once passed through channel 203, the oxygen exits the distal end of handle 224 via aperture 204 and flows down the longitudinal length of insertion guide 220 and ETT 10, facilitating the performance of one or more apneic oxygenation techniques with ETT 10 remaining positioned within the tracheal opening.

FIG. 14 is a plan, cross-sectional view of handle 224 of the preferred insertion guide 220 taken along lines A-A as illustrated in FIG. 13. As described above, notch 230 is preferably formed in the bottom portion of handle 224 to facilitate the efficient removal of stylus 222 from ETT 10, ideally with a single hand of the user. By notching handle 224 as illustrated, the frictional forces biding handle 224 when engaged with ETT 10 are lessened. Further, preferred handle 224 may define one or more protuberances 234 formed on the inner geometry of handle 224. In one embodiment, protuberance 234 defines an annular geometry extending around the inner circumference of handle 224. In this embodiment, O-ring 232 may compress between a top surface of the ETT and protuberance 234. In another embodiment, a pair of protuberances 234 are formed within handle 224. In such an embodiment, O-ring 232 may reside between said protuberances 234. A modification to this embodiment may be that a notch or channel is formed within the inner wall of the body of handle 224, such that the O-ring 232 resides therein, and the O-ring 232 serves as the protuberance, extending inwardly from the body of handle 224 to mate with the top portion of ETT 10. A further embodiment of handle 224 may include no O-ring at all, and instead rely solely on one or more protuberances 234, for example formed from the same material as handle 224. Additionally, or in the alternative, protuberance 234 may define a different geometry, reducing the surface area of handle 224 contracting ETT 10 so as to reduce the coefficient of friction between the same.

The foregoing description of exemplary embodiments of the present invention discloses a novel, non-obvious and useful insertion guide for insertion of an endotracheal tube (ETT), a combination ETT and insertion guide, and a method for facilitating insertion of an ETT into the trachea of a patient. However, it should be noted and will be readily apparent to, understood and appreciated by those skilled in the art that the drawings, figures, illustrations, examples and exemplary embodiments provided herein are for the purpose of providing a complete, accurate and enabling disclosure of the present invention only and are not intended to limit the scope of the appended claims in any manner. As such, it is envisioned that other structures, mechanisms, configurations, components and movements may be utilized to accomplish the same or similar functions with the same or similar results without departing from the intended scope of the appended claims.

We claim:

1. An insertion guide for facilitating insertion of an endotracheal tube (ETT) into the trachea of a patient, comprising:
    an elongated shaft defining a longitudinal axis and at least one of a radiused portion and an angled portion adjacent a distal end of the insertion guide and a handle including defining a notch and a port, each at a proximal end of the insertion guide, the handle further defining a channel and an aperture, the channel in fluid communication with the port and the aperture, the port and the aperture located at opposing ends of the channel, the notch in communication with the aperture;
    wherein the shaft of the insertion guide is configured for insertion within a hollow, flexible tube of the ETT to guide a distal end of the ETT into the trachea of the patient.

2. The insertion guide according to claim 1, further comprising an O-ring positioned within the handle.

3. The insertion guide according to claim 1, wherein the shaft of the insertion guide comprises a solid metallic core that is encased with a polymeric material.

4. The insertion guide according to claim 1, wherein an outer diameter of the shaft of the insertion guide is less than an inner diameter of the tube of the ETT.

5. The insertion guide according to claim 4, wherein the outer diameter of the shaft of the insertion guide is between about 3 mm and about 5 mm.

6. The insertion guide according to claim 1, wherein the radiused portion of the shaft of the insertion guide has a predetermined curvature that is greater than a curvature of the tube of the ETT adjacent the distal end of the ETT.

7. The insertion guide according to claim 6, wherein the curvature of the radiused portion of the shaft of the insertion guide is selected to be about complementary to the curvature of a larynx in the region of the entrance to the trachea of the patient.

8. The insertion guide according to claim 6, wherein the curvature of the radiused portion of the shaft of the insertion guide ranges between about five degrees (5°) and about seven degrees (7°) relative to the elongated shaft longitudinal axis.

9. The insertion guide according to claim 1, wherein the distal end of the insertion guide protrudes beyond the distal end of the ETT by at least about 25 mm.

10. The insertion guide according to claim 1, wherein the angled portion of the shaft of the insertion guide has a length of at least about 25 mm.

11. The insertion guide according to claim 1, wherein the angled portion of the shaft of the insertion guide has a slope of at least about 0.20.

12. A combination endotracheal tube (ETT) and insertion guide for facilitating insertion of the ETT into the trachea of a patient, comprising:
    an ETT comprising an elongated, generally hollow tube made of a flexible material; and
    an insertion guide comprising a handle defining a notch and a channel in fluid communication with a port and an aperture, the port and the aperture located at opposing ends of the channel, and the notch in communication with the aperture;
    wherein a shaft of the insertion guide defines a longitudinal axis and is provided with a radiused portion having a curvature adjacent a distal end of the insertion guide;
    wherein the relatively rigid shaft of the insertion guide is inserted within the hollow, flexible tube of the ETT such that a curvature of the tube adjacent the distal end of the ETT conforms to the curvature of the shaft adjacent the distal end of the insertion guide; and
    wherein the distal end of the insertion guide protrudes beyond the distal end of the ETT.

13. The combination according to claim 12, wherein the curvature of the radiused portion of the shaft of the insertion guide is selected to be about complementary to the curvature of a larynx in the region of the entrance to the trachea of the patient.

14. The combination according to claim 12, wherein the curvature of the radiused portion of the shaft of the insertion guide ranges between about five degrees (5°) and about seven degrees (7°) relative to the shaft longitudinal axis.

15. The combination according to claim 12, wherein the distal end of the insertion guide protrudes beyond the distal end of the ETT by at least about 25 mm.

16. The combination according to claim 12, wherein the shaft of the insertion guide further comprises an angled portion adjacent the distal end of the insertion guide that serves to guide the tube of the ETT past the epiglottis and into the trachea of the patient.

17. The combination according to claim 16, wherein the angled portion of the shaft of the insertion guide has a length of at least about 25 mm.

18. The combination according to claim 16, wherein the angled portion of the shaft of the insertion guide has a slope of at least about 0.20.

* * * * *